United States Patent [19]
Letsinger et al.

[11] Patent Number: 5,476,930
[45] Date of Patent: Dec. 19, 1995

[54] NON-ENZYMATIC LIGATION OF OLIGONUCLEOTIDES

[75] Inventors: Robert L. Letsinger, Wilmette, Ill.; Sergei M. Gryaznov, San Mateo, Calif.

[73] Assignee: Northwestern University, Evanston, Ill.

[21] Appl. No.: 376,688

[22] Filed: Jan. 23, 1995

Related U.S. Application Data

[63] Continuation of Ser. No. 46,032, Apr. 12, 1993, abandoned.
[51] Int. Cl.⁶ .............................. C07H 1/00; C07H 21/00
[52] U.S. Cl. ...................... 536/25.3; 536/24.33; 536/24.5
[58] Field of Search ................................ 536/25.3, 24.33, 536/24.5

[56] References Cited

U.S. PATENT DOCUMENTS 5,237,016  8/1993  Ghosh et al. .......................... 525/329.4

OTHER PUBLICATIONS

Bischofberger, N. and Wagner, R. W., *Virology*, 3:57–66 (1992) "Antisense approaches to antiviral agents".

Uhlmann, E. et al., *Chemical Reviews*, 90:543–584 (1990) "Antisense Oligonucleotides: A New Therapeutic Principle".

Proceedings, International Conference on Nucleic Acid Medical Applications, Cancun, Mexico (Jan. 26–30, 1993).

Proceedings, International Conference on Nucleic Acid Medical Applications, Cancun, Mexico, pp. 59–63 (Jan. 1993).

Woolf, C. M. et al., *Proc. Natl. Acad. Sci. USA*, 89:7305–7309 (1992) "Specificity of antisense oligonucleotides in vivo".

Naylor, R.; Gilham, P. T. *Biochemistry*, 5:2722–2728 (1966) "Studies on Some Interactions & Reactions of Oligonucleotides in Aqueous Solution".

Sokolova, N. I. et al., *FEBS Letters*, 232:153–155 (1988) "Chemical reactions within DNA duplexes".

Shabarova, Z. A. *Biochimie*, 70:1323–1334 (1988) "Chemical development in design of oligonucleotide probes for binding to DNA and RNA".

Kool, E. T., *J. Am. Chem. Soc.*, 113:6265–6266 (1991) "Molecular Recognition by Circular Oligonucleotides: Increasing Selectivity of DNA Binding".

Ashley, G. W.; Kushlan, D. M. *Biochemistry*, 30:2927–2933 (1991) "Chemical Synthesis of Oligodeoxynucleotide Dumbbells".

Luebke, K. J. et al, *J. Am. Chem. Soc.*, 113:7447–7448 (1991) "Nonenzymatic Sequence–Specific Ligation of Double–Helical DNA".

Luebke, K. J. et al., *Nucleic Acids Res.*, 20:3005–3009 (1992) "Nonenzymatic ligation of double–helical DNA by alternate–strand triple helix formation".

Prakash, G.; Kool, E. T., *J. Am. Chem. Soc.*, 114:3523–3527 (1992) "Structural Effects in Recognition of DNA by Circular Oligonucleotides".

Purmal, A. A. et al., *Nucleic Acids Res.*, 20:3713–3719 (1992) "A new affinity reagent for site–spec., covalent attc. of DNA to active–site nucleophiles: appl. to EcoR1 and Rsrl . . .".

Gryaznov, S. M.; Letsinger, R. L., *J. Am. Chem. Soc.*, 115:3808–3809 (1993) "Chemical Ligation of Oligonucleotides in Presence and Absence of a Template".

Goodwin, J. T.; Lynn, D. G. *J. Am. Chem. Soc.*, 114:9197–9198 (1992) "Template–Directed Synthesis: Use of a Reversible Reaction".

Gryaznov, S. M., Letsinger, R. L. *Nucleic Acids Res.*, 20:3403–3409 (1992) "Syntheses & properties of oligonucleotides containing aminodeoxythymidine units".

Thuong, N. T. et al., *Terrahedron Lett.*, 28:4157–4160 (1987) "Synthese et Reactivite D'Oligothymidylates Substitutes Par un Agent Intercalant et un Group Thiophosphate".

Francois, J–C. et al., *Proc. Natl. Acad. Sci. USA*, 86:9702–9706 (1989) "Seq.–specific recog. and cleavage of duplex DNA via triple–helix formation by oligonucleotides covalently . . .".

Beukers, R. et al., *Recueil.*, 77:729–732 (1958) "The Effect of Ultraviolet Light on Some Components of Nucleoic Acids".

Letsinger, R. L. et al., *J. Am. Chem. Soc.* 87:2945–2953 (1965) "Photoinduced Substitution. II. Substitute Effects in Nucleophilic Displacement on Substituted Nitrobenzenes".

Mag, M. et al., *Nucleic Acids Res.*, 19:1437–1441 (1991) "Synthesis & selective cleavage of oligodeoxynucleotide cont. bridged internucleotide 5'-phosphorothioate linkage".
Letsinger, R. L. et al., *Proc. Natl. Acad. Sci. USA*, 86:6553–6556 (1989) "Cholesteryl–conjugated oligonucleotides: Synthesis, properties, & activ. as inhibitors of replication".
Alberts et al. Molecular Biology of the Cell. Garland Publishing, Inc. New York 1983, p. 187.

*Primary Examiner*—Douglas W. Robinson
*Assistant Examiner*—Gary L. Kunz
*Attorney, Agent, or Firm*—Reising, Ethington, Barnard and Perry

[57]     ABSTRACT

A process for non-enzymatic convalent ligation of two oligonucleotides having the structure shown below:

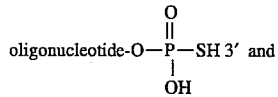

-continued

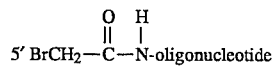

The spontaneous reaction of these above oligonucleotides produces a thiophosphorylacetylamino linkage as shown below:

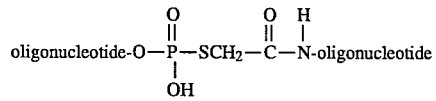

When carried out in the presence of a template, this reaction gives 90% yields within 20 minutes at micromolar concentrations.

7 Claims, 2 Drawing Sheets

NON-ENZYMATIC LIGATION OF OLIGONUCLEOTIDES

This is a continuation of application Ser. No. 08/046,032 filed on Apr. 12, 1993, now abandoned.

TECHNICAL FIELD

The present invention relates to a method of forming oligonucleotides and more specifically to methods having use as potential new therapeutic methods for treating viral diseases, cancer, genetic disorders and the like, as well as diagnostic applications of oligonucleotides.

BACKGROUND OF THE INVENTION

Antisense oligonucleotides have demonstrated potential as new types of therapeutic agents for treating such diseases and disorders as viral diseases, cancer, genetic disorders, as well as other diseases and disorders[1]. Extensive research has been carried out and is being continued in industrial and academic laboratories to explore this potential[2].

A problem that has been encountered with the approach of utilizing antisense oligonucleotides as therapeutic agents is related to the selectivity of the agents in vivo. In view of the low concentrations of intracellular polynucleotide targets and the low concentrations of therapeutic oligonucleotides that can be introduced into cells, it is recognized that there is a need for oligonucleotides with high binding affinities. The binding affinity is related to the length of the oligonucleotides, preferably 20-mers and longer. But, in the case of long oligonucleotides, a mismatch in base pairing is less destabilizing then in the case of a short oligonucleotide. Hence, the desired destabilizing effect is lessened by the use of longer oligonucleotides while the selectivity is increased.

Experts have noted that "high sequence specificity" and "high affinity" are contradictory demands[3]. It has further been concluded that on the basis of the extent to which antisense oligonucleotides can cause cleavage of RNAs at imperfectly matched target sites, in systems that were tested it was probably not possible to obtain specific cleavage of an intended target RNA without also causing at least the partial destruction of many non-targeted RNAs[4]. Hence, experts in the field, based on conducted research, have concluded that the conflicting requirements of specificity and affinity are major hurdles to overcome. Several methods have been reported for covalently linking oligonucleotide blocks in aqueous media[5a-l]. All of these methods require an additional chemical agent to yield a stable ligated product. Depending on the approach, the added reagent may be an "activating agent" such as a water soluble carbodiimide or cyanoimidazole[5a-k] or it may be a reducing agent such as sodium cyanoborohydride[5l]. In either case, the need for the third reagent precludes chemical ligation in vivo since such compounds are toxic, react with water, and could not be introduced into living systems in sufficient amounts to bring about the desired coupling reaction.

The present invention provides a novel method for covalently linking oligonucleotide blocks present in low concentrations in an aqueous medium without need for an additional condensing or stabilizing reagent. It therefore opens the door for in situ chemical ligation in living systems. Since the reactions are greatly accelerated in the presence of a complementary oligonucleotide sequence, one should in principle be able to form long oligonucleotide strands selectively in vivo when a target polynucleotide (e.g. m-RNA or DNA from a virus or cancer cell) containing consecutive nucleotide sequences complementary to the individual oligonucleotide strands is present. Long oligonucleotide strands, which bind with high affinity, would therefore be generated in situ from shorter strands that bind with lower affinity, when the target polynucleotide is present. This invention could therefore solve the problem of the conflict of achieving high affinity as well as high specificity, in therapeutic and also in diagnostic applications.

SUMMARY OF THE INVENTION

In accordance with the present invention there is provided a method of forming an oligonucleotide by irreversibly covalently linking at least two oligomers which themselves are reversibly bound by hydrogen bonding at adjacent positions on a target polynucleotide containing a nucleoside base sequence complementary to the sequences of the pair of oligomers, wherein one of the oligonucleotides includes a nucleotide having a first reactive group adjacent to a nucleotide of the other oligomer which includes a second reactive group capable of spontaneously forming a covalent bond with the first reactive group. The oligonucleotides are covalently joined together through the first and second reactive groups having been brought into proximity to each other upon binding of the oligonucleotides on the polynucleotide.

The present invention further provides a method of forming an oligonucleotide by disposing at least two oligonucleotides in aqueous solution wherein one of the oligonucleotides includes an α-haloacyl group and the other nucleotide includes a phosphothioate group. The oligonucleotides are covalently bound together through the α-haloacyl group and the phosphothioate group spontaneously forming a thiophosphorylacetylamino group therebetween.

BRIEF DESCRIPTION OF THE FIGURES

Other advantages of the present invention will be readily appreciated as the same becomes better understood by reference to the following detailed description when considered in connection with the accompanying drawings wherein.

DETAILED DESCRIPTION OF THE INVENTION

Figure 1:
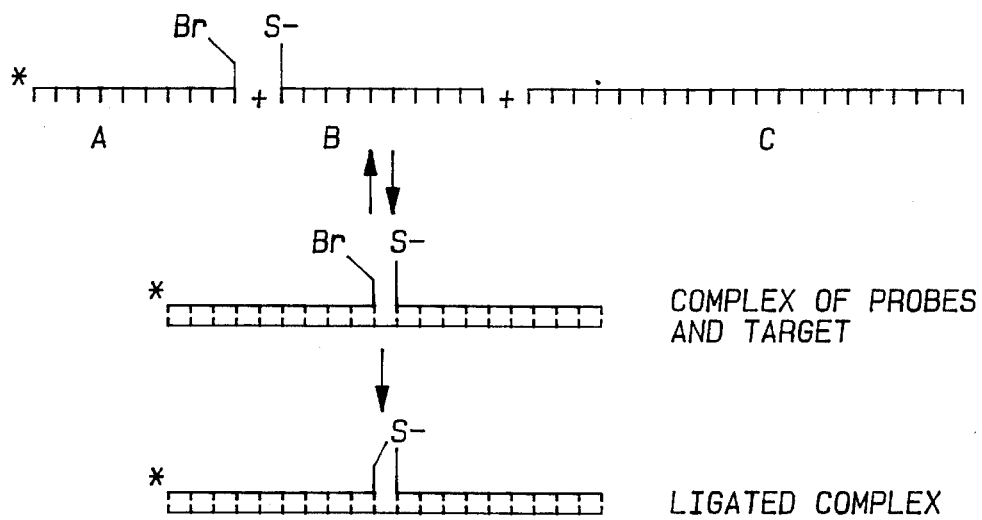
FIG. 1 shows the coupling of two short oligomers in accordance with the present invention utilizing a target template.

In accordance with the present invention there is provided a method of forming an oligonucleotide generally by the steps of disposing at least two oligonucleotides in aqueous solution wherein one of the oligonucleotides includes an α-haloacyl group and the other of the nucleotides includes a phosphothioate group and then covalently binding the oligonucleotides together through the α-haloacyl group and the phosphothioate groups spontaneously forming a thiophosphorylacetylamino group therebetween.

This method exploits the fact that the coupling reaction described herein is very slow in very dilute aqueous solutions but is fast in the presence of a template polynucleotide. That is, the reaction is accelerated in the presence of a target polynucleotide that possesses the sequence section complementary to the probe oligomers. The present invention employs as a therapeutic agent two short oligomers (for example, 8 to 20-mers) which will spontaneously link together covalently after binding at adjacent positions on the target polynucleotide. With this system, one will approach the binding affinity and recognition properties of a longer oligomer probe such as between 16 to 40-mer, but retain the dependency and base pairing characteristics of the shorter probes (8 to 20-mer). In other words, the present invention provides the specificity of shorter polynucleotides while possessing the effect of longer polynucleotides.

Inherent in the present invention is the need and use of polynucleotides including reactive groups which will spontaneously react to form a covalent bond therebetween when the groups are in spacial proximity to each other. Specifically, the present invention utilizes at least two oligonucleotides wherein one set of oligonucleotides includes the first reactive group and the second set of oligonucleotides include the second reactive group such that upon being brought in proximity to each other, the groups will spontaneously react to form a stable covalent bond. Examples of such pairs of reactive groups are ester+hydrazide,RC(O)S$^-$ +haloalkyl and RCH$_2$S$^-$+α-haloacyl. Preferably, the present invention utilizes an α-haloacyl group, such as a bromoacetylamino group and a thiophosphoryl group, which form a thiophosphorylacetylamino bridge efficiently, selectively, and irreversibly in dilute aqueous media. As demonstrated below, the products are stable in water and hybridize well with complementary polynucleotides.

At low oligomer concentrations, such as less than 1 μM, and in absence of a complementary template the reactions are very slow but can be carried out to high conversion within a few days by freezing the solution. The freezing techniques are described in detail below. Coupling is quite fast (greater than 90% conversion in 20 minutes) when carried out in solution in the presence of a complementary oligonucleotide that serves as a template, as shown below in the Example section.

Selectivity is also a major concern in diagnostic applications of the present invention and generally in the use of oligonucleotides. The same features of the present invention that make the novel chemistry of the present invention attractive for therapeutic applications also make it attractive for diagnostic uses. For example, the present invention could be utilized in a diagnostic system as follows.

Referring to FIG. 1, A is an oligomer consisting of, for example, a 10-mer bearing a marker (*) in the chain and a bromoacetylamino group at the 3'-terminus. B is another short oligomer with a thiophosphoryl group at the 5' end. C is a target oligonucleotide sequence with a sequence complementary to A+B. If in dilute solution the coupling of A and B is sufficiently slow in absence of the template, relative to coupling in the presence of the template, only coupling on the template will be significant. This chemical ligation system could therefore be employed in amplification and detection analogously to the enzymatic ligation system (Ligase Chain Reaction, or LCR). It has the potential to be superior since some non-specific coupling introduces a source of error in the enzymatic scheme. The fact that at very low concentrations of oligonucleotides (that is, in the range of interest in diagnostic applications) the rate of the chemical ligation in absence of template becomes extremely slow indicates that the non-template directed coupling could be unimportant in this case.

EXAMPLES

Figure 2:
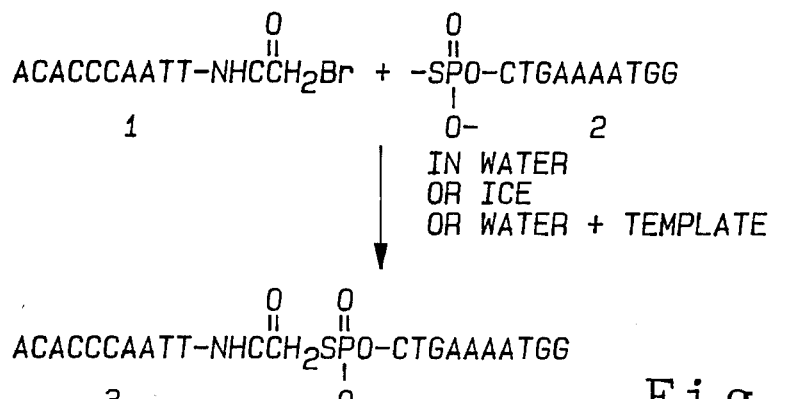
FIG. 2 shows the facile reaction of an oligonucleotide phosphorothioate with an α-haloacyl oligonucleotide derivative in accordance with the present invention.

As shown in FIG. 2, the ligation indicated in equation 1 for oligomers 1 and 2 exploits the facile reaction of a phosphorothioate with an α-haloacyl derivative.

Specifically, compound 1 (Seq. I.D. 1) in FIG. 2 has a 3'-(bromoacetylamino)-3'-deoxythymidine unit at the 3'-terminus. For preparation of compound 1, 15 μL of 0.4M aqueous N-succinimidyl bromoacetate (obtained from Calbiochem) was added to 4.9 A$_{260}$ units of the 3'-aminodeoxyribooligonucleotide precursor, ACACCCAATT-NH$_2$. The method of preparation is described by Gryaznov et al., 1992[6]. The reaction was carried out in 10 μL of 0.2M sodium borate buffer at room temperature. After 35 minutes, the mixture was diluted with 0.5 mL of water, desalted by gel filtration on a NAP-5 column (produced by Pharmacia), and purified by RP HPLC high pressure liquid chromatography and again desalted, giving 4 A$_{260}$ units of compound 1. The elusion times are as follows: RP HPLC, 17.4 minutes; IE HPLC, 17.4 minutes.

The IE HPLC carried out above and all similar procedures carried out below was carried out on a Dionex Omni Pak NA100 4×250 mm column at pH 12 (10 mM sodium hydroxide) with a 2% per minute gradient of 1.0M sodium chloride in 10M sodium hydroxide. For RP HPLC, a Hypersil ODS column (4.6×200 mm) was used with a 1% per minute gradient of acetonitrile in 0.03M triethylammonium acetate buffer at pH 7.0.

Compound 2 (Seq. I.D. 2) was synthesized on a 1 μmole scale on a Milligen/Biosearch Cyclone DNA Synthesizer using LCAA CPG supported 5'-dimethoxytrityl-N-isobutyryldeoxyguanosine. Standard cyanoethyl phosphoramidite chemistry was used. When chain elongation was complete, the terminal 5'-hydroxyl group was phosphitilated (5 minutes) with 150 μL of a 0.1M solution of "Phosphate ON$^{TM}$" reagent (from Cruachem) in acetonitrile and 150 μL of 0.5M tetrazole in acetonitrile. The resulting phosphite was sulfurized by treatment with a 5% solution of sulfur in pyridine/carbon disulfide (1:1, v/v, 45 minutes at room temperature). After cleavage of the DMT group (3% DCA in dichloromethane, 1.5 minutes) the supported polymer was worked up as in the case of compound 1.

Reaction of a thiophosphoryloligonucleotide with a haloacetylaminoaromatic derivative in DMS and water has been employed in preparing dye-oligonucleotide conjugates[7].

Depending upon the use of the invention and the desired kinetics, coupling of the oligonucleotides can be carried out in either aqueous solution, in a frozen state in ice, or in an aqueous solution in the presence of template, as discussed above and as exemplified below.

Figures 3A, 3B, 3C:
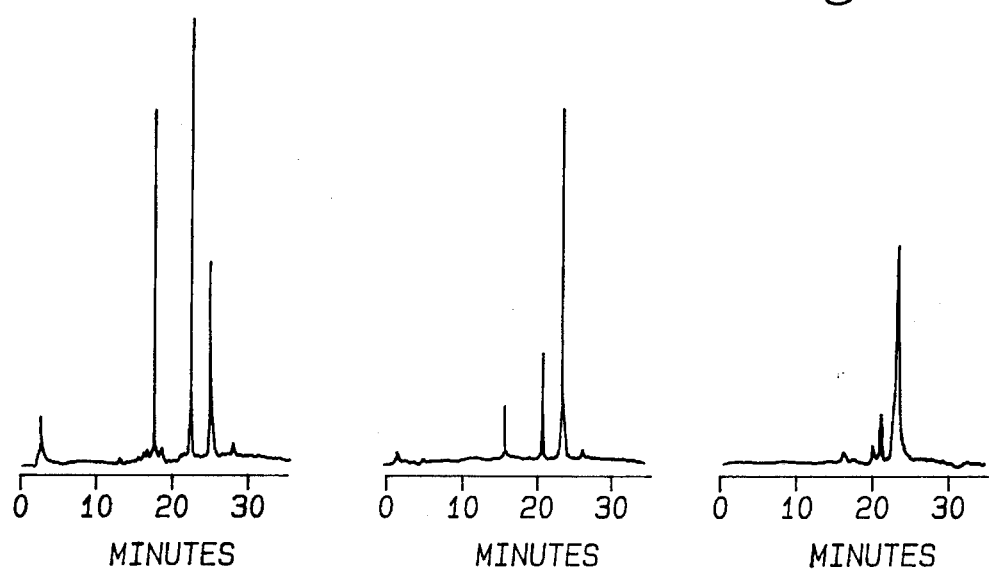
FIG. 3 shows results of ion exchange high performance liquid chromatography (IE HPLC) of products from experiment 1 wherein: A, after 2 hours in solution at 0° C.; B, after 2 days at 0° C.; and C, after the final step in which the solution was frozen and stored at −18° C. for 5 days, the peaks at approximately 17, 21 and 24 minutes correspond to compounds (seq. I.D. 1), 2 (Seq. I.D. 2), and 3 (Seq. I.D. 3), respectively.

In an initial experiment, 1.0 mL of a solution (pH 7.05, 15 mM phosphate, 85 mM NaCl) containing compounds 1 (0.39 $A_{260}$ units, 4 μM) and 2 (0.41 $A_{260}$ units, 4 μM) was prepared and kept at 0° C. for 5 days. The solution was warmed to 50° C. for 2.5 hours, and finally frozen and stored at −18° C. for an additional 5 days. Analysis by IE HPLC of samples after 2 hours and 48 hours showed formation of a slower eluting product, oligomer 3 (FIG. 2), in yields of about 25% and 80%, respectively. No significant change was observed after the additional 3 days at 0° C. or warming at 50° C. However, the reaction did proceed further in the frozen state, affording a high conversion to compound 3 (Seq. I.D. 3) within 5 days as shown in FIG. 3. The enhanced extent of reaction in the ice matrix may be attributed to the high local concentration of the oligonucleotide reactants within the cavities in the ice. Other reactions have been similarly carried out in an ice matrix[8].

Figures 4A, 4B, 4C:
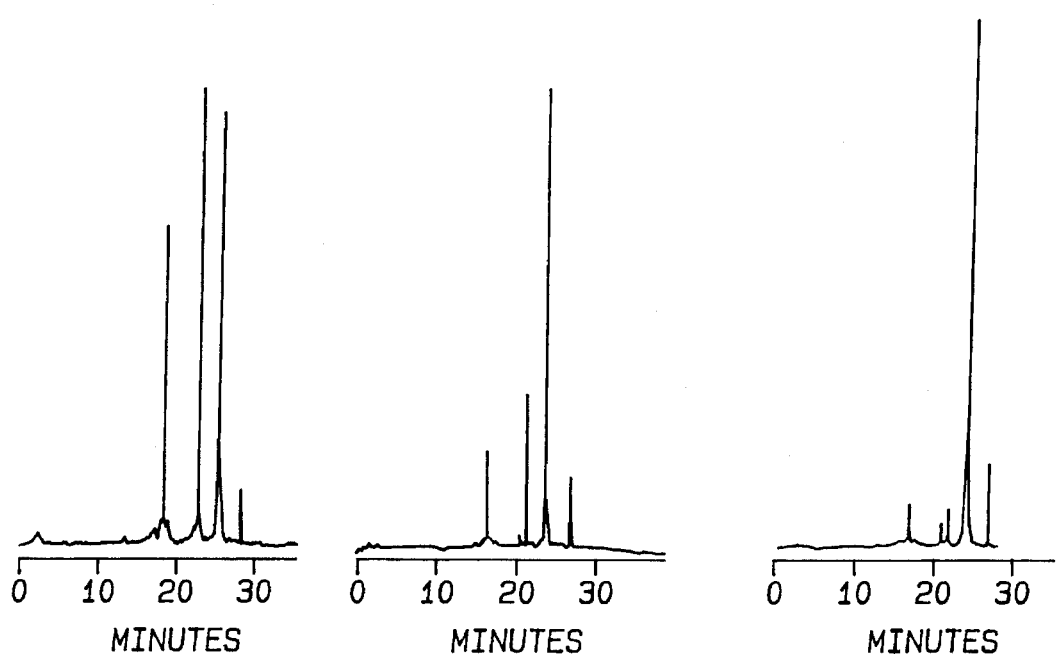
FIG. 4 shows IE HPLC of products from a second experiment (frozen, −18° C. throughout) after: wherein A, after 2 hours in solution at 0° C.; B, after 2 days at 0° C.; and C, after: A, 5 hours; B, 2 days; and C, 5 days, the peaks at approximately 17, 21, and 24 minutes corresponding to compounds 1, 2, and 3, the peak at 27 minutes corresponding to the dimer derivative of compound 2 produced by oxidation by air.

In light of this result, an equimolar mixture of compounds 1 and 2 (2 μM each) in the same buffer was directly frozen and held at −18° C. The HPLC profiles obtained from samples after 5 hours and daily thereafter show progression to give a high yield of 3 in 5 days, FIG. 4 showing representative data.

Data for coupling compounds 1 and 2 in solution in the presence of a complementary oligonucleotide template (CCATTTTCAGAATTGGGTGT, compound 4, Seq. I.D. 4) are presented in FIG. 5. The system was the same as in the first experiment except template 4 was also present (4 μM). In this case the reaction proceeded to >90% completion within 20 minutes and was essentially complete within 2 hours.

The structure assigned to compound 3 is supported by the properties of a model compound (T—NHC(O)CH$_2$—SP(O)(O$^-$)O—T, prepared in solution on a larger scale than used for compound 3), by the mobility of compound 3 on gel electrophoresis (Rm 0.58, compared to Rm 0.89, 0.95, and 0.61 for compounds 1,2, and 4, respectively),and by the stability of the complex formed with the complementary oligonucleotide, 4. Retention time, RP HPLC 10.5 minutes; FAB$^+$ mass spectrum, M+H$^+$ 620, M+Na$^+$ 642; $^{31}$p NMR, β in D$_2$O, 18.7 ppm, prior references have disclosed characteristics for the alkylthiophosphate group.[9]

Figures 5A, 5B:
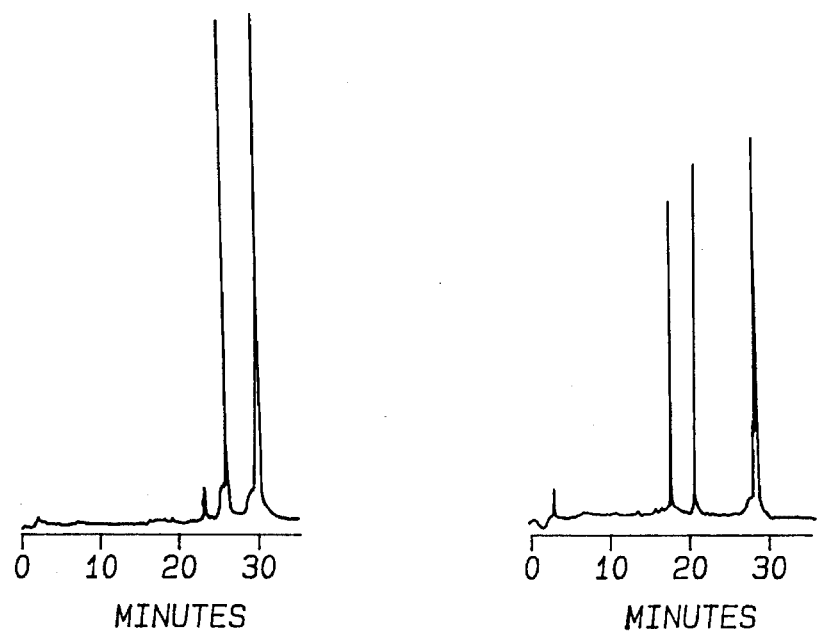
FIG. 5 shows the following: A, IE HPLC of products from the reaction of compounds 1 and 2 in presence of template 4 at 0° C. after 2 hours, the major peaks corresponding to coupling product 3 and template 4, noting that compound 1 (peak at 17 minutes) has been almost completely consumed; B, same products after treatment with $KI_3$ followed by Dithiothreitol (DTT); noting that compound 3 has been replaced by two oligonucleotide cleavage products, eluting at 18 and 22 minutes.

Rm values are relative to bromophenol blue in a 20% polyacrylamide/5% bis acrylamide gel. The Tm value, 56° C. in 0 1M NaCl, approaches that of the complex formed from the corresponding all-phosphodiester 20-mer and compound 4 (60° C.)[10] and differs significantly from values for complexes formed from compounds 1 or 2 with compound 4 (37° C. and 31° C.). In addition, the internucleotide —NH(CO)CH$_2$SP(O)(O_)— link was found to be cleaved selectively on oxidation with KI$_3$[9] (FIG. 5). More specifically, the duplex containing compounds 3 and 4 (0.3 $A_{260}$ units each) in 100 μL of water was treated with 100 μL of 0.2 M aq. KI$_3$ for 15 minutes at 50° C. Then 10 μL of 1 M aq. DTT was added to the solution. After 5 minutes the mixture was desalted on a NAP-5 column and analyzed by IE HPLC.

The above experimentation provides evidence that the present invention presents novel chemistry which provides a convenient means for selectively and irreversibly coupling oligonucleotides in aqueous solution in the range of 4 μM oligomer concentration or greater. The products have been shown to be stable in neutral solution and for a few hours even at pH 12 at room temperature. At concentrations below 1 μM, the rate in the liquid phase become extremely slow. However, the reactions can be carried to near completion in the frozen state. The rate of coupling is markedly accelerated by the presence of a complementary oligonucleotide template. These properties provide a potential in the design of chemical amplification systems and in situ ligation in antisense application as well as in building complex structures from oligonucleotide blocks based on known chemistry.

The invention has been described in an illustrative manner, and it is to be understood that the terminology which has been used is intended to be in the nature of words of description rather than of limitation.

Obviously many modifications and variations of the present invention are possible in light of the above teachings.

REFERENCES 1. (a) Bischofberger, N. and Wagner, R. W. "Antisense Approaches to Antiviral Agents" *Virology*, 3, 57–66 (1992). (b) Uhlmann, E. and Peyman, A. "Antisense Oligonucleotides: A New Therapeutic Principle" *Chemical Reviews*, 90, 543–584 (1990).
2. Proceedings, International Conference on Nucleic Acid Medical Applications, Cancun, Mexico, Jan 26–30, 1993; P.O.P. Ts'o and P. S. Miller, Organizers, John Hopkins University, Baltimore, Md.
3. Proceedings, International Conference on Nucleic Acid Medical Applications, Cancun, Mexico, January, 1993, pg. 60.
4. Woolf, T. M., Melton, D. A., and Jennings, D. G. B. Proc. Natl. Acad. Sci. USA 89, 7305–7309 (1992).
5. (a) Naylor, R.; Gilham, P. T. *Biochemistry* 1966. 5, 2722–2728. (b) Sokolova, N. I.: Ashirbekova, D. T.; Dolinnaya, N. G.; Shabarova, Z. A. *FEBS Letters* 1988, 232, 153–155. (c) Shabarova, Z. A. *Biochemic* 1988, 70, 1323–1334. (d) Chu, B. C. F.; Orgel, L. E. *Nucleic Acids Res.* 1988, 16, 3671–3691. (e) Kool, E. T. *J. Am. Chem. Soc.* 1991, 113, 6265–6266. (f) Ashley, G. W.; Kushlan, D. M. *Biochemistry* 1991, 30, 2927–2933. (g) Luebke, K. J.; Dervan, P. B. *J. Am. Chem. Soc.* 1991, 113, 7447–7448. (h) Luebke, K. J.; Dervan, P. B. *Nucleic Acids Res.* 1992, 20, 3005–3009. (i) Prakask, G.; Kool, E. T. *J. Am. Chem. Soc.* 1992, 114, 3523–3527. (j) Purmal, A. A., Shabarova, Z. A.; Gumport, R. I. *Nucleic Acids Res.* 1992, 20, 3713–3719. (k) Gryaznov, S. M.; Letsinger, R. L., in press, *Nucleic Acids Res.* (l) Goodwin, J. T.; Lynn, D. G. *J. Am. Chem. Soc.* 1992, 114, 9197–9198.
6. Gryaznov, S. M., Letsinger, R. L. *Nucleic Acids Res.*, 1992, 20, 3403–3409.
7. (a) Thuong, N. T.; Chassignol, M. *Terrahedron Lett.* 1987, 28, 4157–4160. (b) Francois, J. C.; Saison-Behmoaras, T.; Barbier, C.; Chassignol, M.; Thoung, N. T.; Helene, C. *Proc. Natl. Acad. Sci. USA* 1989, 86, 9702–9706.
8. (a) Beukers, R.; Ylstra, J.; Berends, W. *Rec. Tray. Chim.* 1958, 77, 729–732. (b) Letsinger, R. L.; Ramsay, O. B.; McCain, J. H. *J. Am. Chem. Soc.* 1965, 87, 2945–2953.
9. Mag, M.; Luking, S.; Engels, J. W. *Nucleic Acids Res.* 1991, 19, 1437–1441.
10. Letsinger, R. L.; Zhang, G.; Sun, D. K.; Ikeuchi, T.; Sarin, P. S. *Proc. Natl. Acad, Sci. USA* 1989, 86, 6553–6556.

What is claimed is:

1. Method of forming an oligonucleotide by:
   a) reversibly binding at least two oligonucleotides at adjacent positions on an oligo- or polynucleotide including base units complementary to base units of the oligomers, wherein one of the oligonucleotides includes a nucleotide having a first reactive group with a 3' or 5' terminal bromoacetylamino proximate to a nucleotide of the other oligomer which having a second reactive group includes a 3' or 5' terminal phosphorothioate capable of spontaneously forming a covalent bond with the first reactive group; and
   b) irreversibly covalently joining the oligonucleotides together through the first and second reactive groups having been brought in proximity to each other upon binding of the oligonucleotides on the polynucleotide in the absence of added reagent or enzyme to spontaneously form a thiophosphorylacetylamino bond through the reactive groups.

2. A method of forming an oligonucleotide of claim 1 wherein each of the oligomers consists of 8 to 20 nucleotides.

3. A method of forming an oligonucleotide of claim 1 wherein steps (a) and (b) occur in aqueous solution.

4. A method of forming an oligonucleotide by:
   a) disposing at least two oligonucleotides in aqueous solution wherein one of the oligonucleotides has a 3' or 5' terminal bromoacetylamino group and the other of the nucleotides has a 3' or 5' terminal phosphorothioate group; and
   b) covalently binding the oligonucleotides together through the α-haloacyl group and the phosphothioate groups spontaneously forming a thiophosphorylacetylamino group therebetween.

5. A method of forming an oligonucleotide of claim 4 further including the step of (c) accelerating the reaction and carrying the reaction out to high completion by freezing the aqueous solution containing the oligonucleotides therein.

6. A method as set forth in claim 1 wherein the structure of the oligonucleotides is

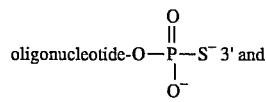 and

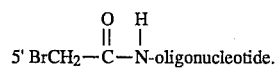

7. A method as set forth in claim 1 wherein the structure of the oligonucleotides is

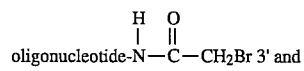 and

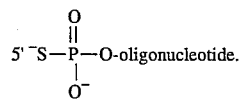

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: both
        ( D ) TOPOLOGY: both ( i i ) MOLECULE TYPE: DNA (genomic)

( i x ) FEATURE:
        ( A ) NAME/KEY: misc_difference
        ( B ) LOCATION: replace(1..11, "")
        ( D ) OTHER INFORMATION: /note="N is a bromoacetylamino group"

( x i ) SEQUENCE DESCRIPTION: SEQ ID NO:1:

ACACCCAATT N                                        11

( 2 ) INFORMATION FOR SEQ ID NO:2:

( i ) SEQUENCE CHARACTERISTICS:
        ( A ) LENGTH: 11 base pairs
        ( B ) TYPE: nucleic acid
        ( C ) STRANDEDNESS: both
        ( D ) TOPOLOGY: both ( i i ) MOLECULE TYPE: DNA (genomic)

( i x ) FEATURE:
        ( A ) NAME/KEY: misc_difference
        ( B ) LOCATION: replace(1..2, "")
        ( D ) OTHER INFORMATION: /note="N is a thiophosphoryl group"

( x i ) SEQUENCE DESCRIPTION: SEQ ID NO:2:

NCTGAAAATG G                                        11

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: both ( i i ) MOLECULE TYPE: DNA (genomic)

( i x ) FEATURE:
        ( A ) NAME/KEY: misc_difference
        ( B ) LOCATION: replace(11..12, "")
        ( D ) OTHER INFORMATION: /note="NN is a thiophosphorylacetylamino group"

( x i ) SEQUENCE DESCRIPTION: SEQ ID NO:3:

ACACCCAATT NNCTGAAAAT GG                         22

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: both ( i i ) MOLECULE TYPE: DNA (genomic)

( i x ) FEATURE:
    ( A ) NAME/KEY: misc_feature
    ( B ) LOCATION: 1..20
    ( D ) OTHER INFORMATION: /note="Complementary to Seq. 3
       without NN"

( x i ) SEQUENCE DESCRIPTION: SEQ ID NO:4:

CCATTTTCAG AATTGGGTGT                    20